United States Patent
Grinstein et al.

(10) Patent No.: US 11,967,435 B2
(45) Date of Patent: Apr. 23, 2024

(54) MODELING OF FLOW THROUGH A LEFT VENTRICULAR ASSIST DEVICE (LVAD)

(71) Applicants: MEDSTAR HEALTH, INC., Columbia, MD (US); UCL BUSINESS LTD., London (GB); BARTS HEALTH NHS TRUST, London (GB)

(72) Inventors: Jonathan Grinstein, Chicago, IL (US); Hector Manuel Garcia Garcia, Chevy Chase, MD (US); Christos Bourantas, London (GB); Ryo Torii, London (GB)

(73) Assignees: MEDSTAR HEALTH, INC., Columbia, MD (US); UCL BUSINESS LTD., London (GB); BARTS HEALTH NHS TRUST, London (GB)

( * ) Notice: Subject to any disclaimer, the term of this patent is extended or adjusted under 35 U.S.C. 154(b) by 0 days.

(21) Appl. No.: 17/434,497

(22) PCT Filed: Feb. 28, 2020

(86) PCT No.: PCT/US2020/020328
§ 371 (c)(1),
(2) Date: Aug. 27, 2021

(87) PCT Pub. No.: WO2020/176840
PCT Pub. Date: Sep. 3, 2020

(65) Prior Publication Data
US 2022/0044825 A1 Feb. 10, 2022

Related U.S. Application Data

(60) Provisional application No. 62/811,606, filed on Feb. 28, 2019.

(51) Int. Cl.
*A61M 60/178* (2021.01)
*A61B 8/06* (2006.01)
(Continued)

(52) U.S. Cl.
CPC ............... *G16H 50/70* (2018.01); *A61B 8/06* (2013.01); *A61M 60/178* (2021.01);
(Continued)

(58) Field of Classification Search
CPC ........ A61B 8/06; A61M 60/178; G16H 30/20
See application file for complete search history.

(56) References Cited

U.S. PATENT DOCUMENTS

2003/0032853 A1 2/2003 Korakianitis et al.
2010/0280352 A1* 11/2010 Ionasec ............... G06N 7/005
600/407
(Continued)

FOREIGN PATENT DOCUMENTS

WO    WO-2019195783 A1 * 10/2019    ......... A61B 5/02035

OTHER PUBLICATIONS

Grinstein et al., Left Ventricular Assist Device Flow Pattern Analysis Using a Novel Model Incorporatin Left Ventricular Pulsatility, 2021, ASAIO Journal, 67; p. 724-733. (Year: 2021).*
(Continued)

*Primary Examiner* — Rex R Holmes
*Assistant Examiner* — Jennifer L Ghand
(74) *Attorney, Agent, or Firm* — TAROLLI, SUNDHEIM, COVELL & TUMMINO L.L.P.

(57) ABSTRACT

A model of flow through a left ventricular assist device (LVAD) can be used for preoperative planning of implantation of the LVAD into a patient and/or optimization of the LVAD after implantation into the patient are described. At least one imaging data set related to a patient and at least one physiological data set related to the patient can be received. An ideal parameter related to the LVAD can be determined based on the at least one imaging data set related to the patient, the at least one physiological data set related to the patient using a model of circulation in a large spatial region (Continued)

A. HEARTMATE II    B. HEARTMATE 3    C. HVAD

D. ARTIFICIAL PULSE OF HM3    E. LAVARE CYCLE OF HVAD of the patient's body and a three-dimensional anatomical model of at least one component of the region of the patient's body and at least one component of the LVAD. Flow patterns within the three-dimensional anatomical model are calculated using computational fluid dynamics.

18 Claims, 8 Drawing Sheets

(51) Int. Cl.
| | |
|---|---|
| *A61M 60/216* | (2021.01) |
| *A61M 60/232* | (2021.01) |
| *A61M 60/515* | (2021.01) |
| *A61M 60/562* | (2021.01) |
| *A61M 60/857* | (2021.01) |
| *G06F 30/28* | (2020.01) |
| *G16H 10/60* | (2018.01) |
| *G16H 20/40* | (2018.01) |
| *G16H 30/20* | (2018.01) |
| *G16H 50/30* | (2018.01) |
| *G16H 50/70* | (2018.01) |
| *G06F 113/08* | (2020.01) |
| *G16H 40/40* | (2018.01) |
| *G16H 40/67* | (2018.01) |

(52) U.S. Cl.
CPC ........ *A61M 60/216* (2021.01); *A61M 60/232* (2021.01); *A61M 60/515* (2021.01); *A61M 60/562* (2021.01); *A61M 60/857* (2021.01); *G06F 30/28* (2020.01); *G16H 10/60* (2018.01); *G16H 20/40* (2018.01); *G16H 30/20* (2018.01); *G16H 50/30* (2018.01); *G06F 2113/08* (2020.01); *G16H 40/40* (2018.01); *G16H 40/67* (2018.01)

(56) References Cited

U.S. PATENT DOCUMENTS

| | | | |
|---|---|---|---|
| 2014/0249791 A1* | 9/2014 | Taylor | A61B 5/004 703/11 |
| 2017/0032097 A1* | 2/2017 | Itu | G16H 50/50 |
| 2017/0112986 A1 | 4/2017 | Heuring et al. | |
| 2017/0136164 A1 | 5/2017 | Yeatts et al. | |
| 2018/0260513 A1* | 9/2018 | Dweik | G06F 30/20 |
| 2019/0183579 A1* | 6/2019 | Kosior | A61B 6/032 |
| 2021/0052328 A1* | 2/2021 | Sengupta | B33Y 80/00 |
| 2021/0193315 A1* | 6/2021 | Lee | G16H 70/20 |

OTHER PUBLICATIONS

Thaker et al., Innovative Modeling Techniques and 3D Printing in Patients with Left Ventricular Assist Devices: A Bridge from Bench to Clinical Practice, May 1, 2019, Journal of Clinical Medicine, p. 2-9. (Year: 2019).*

Shad et al., Patient-Specific Computatonal Fluid Dynamics Reveal Localized Flow Patterns Predictive of Post-Left Ventricular Assist Device Aortic Incompetence, Jul. 2021, Circulation: Heart Failure, vol. 14, Iss. 7, p. 737-745. (Year: 2021).*

Fraser et al., The use of computational fluid dynamics in the development of ventricular assist devices, Apr. 2011, Medical Engineering & Physics, vol. 33 (3), p. 263-280. (Year: 2011).*

Markl et al., Three-dimensional magnetic resonance flow analysis in a ventricular assist device, Dec. 2007, The Journal of Thoracic and Cardiovascular Surgery, vol. 134(6), p. 1471-1476 (Year: 2007).*

PCT Int'l Search Report and Written Opinion, pp. 1-11, dated May 22, 2020.

* cited by examiner

A. HEARTMATE II​​​​​​​​​​​​​​​​​​​​​​B. HEARTMATE 3​​​​​​​​​​​​​​​​​​​​​​C. HVAD

D. ARTIFICIAL PULSE OF HM3​​​​​​​​​​​​​​​​​​​​​​E. LAVARE CYCLE OF HVAD

MODELING OF FLOW THROUGH A LEFT VENTRICULAR ASSIST DEVICE (LVAD)

RELATED APPLICATIONS

This application claims priority to U.S. Provisional Application Ser. No. 62/811,606, filed Feb. 28, 2019, entitled "LVAD CANNULA". The entirety of this provisional application is hereby incorporated by reference for all purposes.

TECHNICAL FIELD

The present disclosure relates generally to modeling flow through a left ventricular assist device (LVAD) and, more specifically, to systems and methods that employ computational modeling of flow through an LVAD that considers the flow patterns within a patient for preoperative planning of implantation of the LVAD into a patient and/or optimization of the LVAD after implantation into the patient.

BACKGROUND

A left ventricular assist device (LVAD) is a durable mechanical pump that provides constant unloading of the left ventricle in patients with advanced heart failure. Currently, LVADs are implanted in over 2,500 patients per year; however, patients with an implanted LVAD have a high risk of experiencing adverse events/complications. Many of the adverse events/complications may be due to improper understanding of the flow through the LVAD. Currently, the flow through the LVAD can be determined based on ex vivo and in vivo modeling using a combination of artificial circuits, computer simulations and animal models, but such studies neglect to examine the flow patterns within a patient supported by an LVAD.

SUMMARY

The present disclosure relates to systems and methods that employ computational modeling of flow through a left ventricular assist device (LVAD) that considers the flow patterns within a patient for preoperative planning of implantation of the LVAD into a patient and/or optimization of the LVAD after implantation into the patient.

In an aspect, the present disclosure can include a system that can model flow through an LVAD. The system includes a non-transitory computer readable medium storing instructions; and a processor configured to access the non-transitory computer readable medium and execute the instructions to at least: receive at least one imaging data set related to a patient and at least one physiological data set related to the patient; and determine an ideal parameter related to a left ventricular assist device (LVAD) based on the at least one imaging data set related to the patient, the at least one physiological data set related to the patient using (1) a model of circulation in a large spatial region of the patient's body and (2) a three-dimensional anatomical model of at least one component of the region of the patient's body and at least one component of the LVAD. Flow patterns within the three-dimensional anatomical model are calculated using computational fluid dynamics (CFD). The ideal parameter is output at least one of an audio output and a visual output.

In another aspect, the present disclosure can include a method for modeling flow through an LVAD. The method is performed by a system comprising a processor. The method includes receiving at least one imaging data set related to a patient and at least one physiological data set related to the patient; and determining an ideal parameter related to a left ventricular assist device (LVAD) based on the at least one imaging data set related to the patient, the at least one physiological data set related to the patient using (1) a model of circulation in a large spatial region of the patient's body and (2) a three-dimensional anatomical model of at least one component of the region of the patient's body and at least one component of the LVAD. Flow patterns within the three-dimensional anatomical model are calculated using computational fluid dynamics (CFD).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "left ventricular assist device (LVAD)" can refer to a mechanical pump that is implanted in patients with heart failure. In operation, the LVAD helps the left ventricle of a patient's heart pump blood out to the aorta and the rest of the body. The mechanical pump can be a pulsatile pump (that uses positive displacement and mimics natural pulsing action of the heart) or continuous flow pumps (that employ a centrifugal pump or an axial flow pump that uses one or more rotors containing permanent magnets that cause the rotors to spin). The LVAD can be a durable device that provides long-term support or a non-durable device that can be used to stabilize a patient as a bridge to recovery, transplant or durable LVAD. The LVAD includes at least an inflow cannula, the pump, and an outflow cannula, such that blood enters the inflow cannula (positioned in the left ventricular apex), through the pump, and out the outflow cannula before re-entering the general circulation in the ascending aorta.

As used herein, the term "inflow cannula" can refer to a tube inserted into the patient's body and positioned in the left ventricular apex to deliver blood to the pump. Two major parameters associated with the inflow cannula include position in the left ventricular apex and angulation. Ideally, the inflow cannula should be positioned parallel to the left ventricular long axis and point toward the mitral valve to maximize flow into the LVAD and minimize mechanical contact and obstruction to flow within the ventricular walls. However, the ideal positioning of the inflow cannula is rarely met. Significant variation exists in surgical technique between different surgeons and there is no consensus on the routine role of intraoperative imaging to guide inflow cannula positioning. Furthermore, remodeling of the left ventricle following decompression of the ventricle following decompression of the ventricle together with neurohormonal blockade often leads to migration of the inflow cannula over time.

As used herein, the term "outflow cannula" can refer to a tube inserted into the patient's body and positioned to deliver blood from the pump to the aorta. Two major parameters associated with the outflow cannula include position of the interface with the aorta and angulation within the interface. The outflow cannula exits the pump and then runs cephalad in the right parasternal space before anastomosing with the aorta. The location of anastomosis, as well as the angle of anastomosis, are important determinants of aortic root blood stagnation, as well as aortic shear stress. The outflow cannula positioning and angle at the time of LVAD implantation is highly variable due to operator variability.

As used herein, the term "flow" can refer to "blood flow", the movement of blood through a patient's body, including through vessels, tissues, and organs.

As used herein, the term "flow pattern" can refer to the way in which fluids, like blood, move through at least a portion of a patient's body.

As used herein, the term "computational fluid dynamics" or "CFD" can refer to a branch of fluid mechanics that simulates and analyzes the interaction of fluids within a defined boundary (e.g., flow patterns in the cardiovascular system). CFD incorporates mathematical equations defining fluid dynamics with structural data to simulate flow (e.g., providing flow parameters including velocity, pressure and shear stress), as well as analyze and solve problems that involve fluid flows.

As used herein, the term "computational modeling" (also referred to as "modeling") can refer to a use of one or more computers to simulate and study the behavior of complex systems using mathematics. An example use of computer modeling is running one or more computer simulations.

As used herein, the term "animal model" can refer to a non-human species used in medical research to mimic at least one biological aspect of a human.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc. As an example, the patient can be a human suffering from advanced heart failure awaiting implantation of an LVAD or with an implanted LVAD.

As used herein, the term "in vivo" can refer to something performed or taking place within a living organism.

As used herein, the term "ex vivo" can refer to something performed or taking place outside a living organism.

II. Overview

Patients with an implanted LVAD have a high risk of morbidity and/or mortality, which is thought to be at least in part due to the anatomical positioning of the LVAD inflow cannula and/or LVAD outflow cannula. Currently, the anatomical positioning of the LVAD inflow cannula and/or LVAD outflow cannula is determined based on ex vivo and in vivo modeling using a combination of artificial circuits, computer simulations and animal models, but such studies neglect to examine the flow patterns within a patient supported by an LVAD. The present disclosure advances over traditional methods of determining parameters related to LVAD implantation by considering the flow patterns within the patient supported by the LVAD, examining a complete hemodynamic and structural assessment of the pump-patient interaction, both for preoperative planning of implantation of the LVAD and for optimization of the LVAD after implantation into the patient. For example, most LVADs deliver continuous flow, but the new flow transmitted to the patient can be pulsatile as a result of a constantly-changing pressure gradient across the LVAD during different stages of the cardiac cycle, irrespective of the presence of the aortic valve opening; the flow patterns within the patient and through the LVAD can take into the pulsatile left ventricle and continuous flow generated by the LVAD, allowing better configuration of the LVAD to account for these differences.

Using the systems and methods of the present disclosure, LVAD cannula positions which are associated with higher rates of blood stagnation, shear stress and patient morbidity can be identified to help guide surgeons about implant techniques and positioning. Optimal (or "ideal") parameters related to implantation of the LVAD, including the location and/or the angle of the inflow cannula and/or the outflow cannula, the speed settings for the LVAD, and the like, can be determined using the models of the flow patterns employed by the systems and methods With the optimal positioning the optimization of shear stress and the reduction of areas of blood stagnation, the rates of post-implant thrombosis, stroke and aortic insufficiency can be reduced dramatically. Additionally, as current and future generations of LVADs become more customizable, the systems and methods will allow users to choose the ideal flow pattern to minimize stagnation and optimize shear stress while maximizing aortic valve opening and unloading.

III. Systems

An aspect of the present disclosure can include a system 10 (FIG. 1) that can model flow through a left ventricular assist device (LVAD). Notably, the system 10 can be used to provide a personalized performance prediction of a cardiovascular system including one or more different LVAD devices. For example, flow through different LVAD devices (or the same LVAD devices with different parameters) can be modeled using the system 10 so that the LVAD device and/or parameters that best fit the patient to be identified, with the goal improving LVAD implantation and use by minimizing the morbidity and mortality of the LVAD implantation and use. The ultimate goal of the system 10 is to ensure that the interplay between the anatomic positioning of the LVAD, as well as one or more operating parameters of the LVAD, and flow through the LVAD can be optimized to enhance the outcomes of patients with LVAD devices by mitigating adverse events for patients with LVAD devices.

Figure 1:
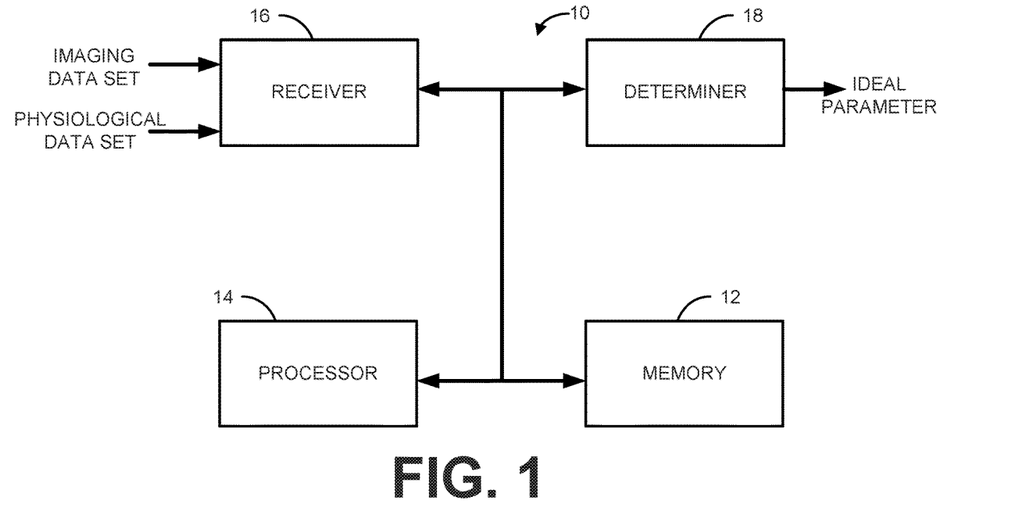
FIG. 1 is a schematic diagram showing an example of a system that can model flow through a left ventricular assist device (LVAD) in accordance with an aspect of the present disclosure.

In operation, the system 10 can input data about the patient and/or the LVAD and output one or more ideal parameters related to the LVAD based on the model of flow. The input data can include at least an imaging data set (e.g., a preoperative data set including pre-operative images, a post-operative data set including post-operative images, a data set including pre-operative images and post-operative images, etc.) and physiological data sets. For example, the at least one imaging data set can be from a computed tomography (CT) scan, which can be a high-resolution CT scan, and the at least one physiological data set can be from an echocardiogram (ECG). In a more specific example, the image data set can include one or more images (e.g., computed tomography images) of at least a portion of a cardiovascular system of the patient (e.g., a heart computed tomography data set) and the physiological data set can include ECG data from the patient (or other data related to the cardiovascular system). Additional data can also be input related to the patient and/or the LVAD (e.g., to increase specificity of the modeling). For example, the data can include one or more hemodynamic parameters/variables, data from a physical examination of the patient, cardiac catheterization data for the patient, or the like. Additionally, although CT images are described, it will be understood that other types of images can be used by the system 10 (in other words, system 10 is not limited to CT images).

In some instances, the ideal parameter can be used for pre-operative planning related to the LVAD. For example, the ideal parameter can guide positioning of components of the LVAD to fit the unique anatomic and physiological needs for a given patient. As another example, the ideal parameter can assist with LVAD selection to help select the proper pump that can best meet the physiologic needs of the patient. In other instances, the ideal parameter can be used for post-implant optimization of the LVAD. For example, the ideal parameter can serve as a virtual ramp-study to optimize device settings at rest or during simulated exercise. It should be noted that the ideal parameter can be a numerical value, a series of numerical values, several series of numerical values, one or more words/sentences, or the like.

For example, the ideal parameter can include a position of an inflow cannula of the LVAD within the patient's body, an angle of the inflow cannula of the LVAD within the patient's body, a location/position of the outflow cannula of the LVAD within the patient's body, an angle of the outflow cannula of the LVAD within the patient's body, and/or at least one parameter related to speed (e.g., fixed speed, asynchronous speed undulation, phasic speed undulation, etc.), pulsatility (e.g., pulsatile or continuous), or the like, associated with the LVAD within the patient's body. As another example, the ideal parameter can indicate a value of concomitant valve surgery (e.g., to predict hemodynamic benefit of surgery, to predict the final morphologic conditions after remodeling, etc.) at the time of implantation of the LVAD. In other instances, the ideal parameter can indicate how flow through the LVAD would be affected through a simulation of exercise.

The system 10 can be implemented by one or more computing devices. For example, the system 10 can be implemented as stand-alone software that can be run at an individual medical facility and receive inputs locally. As another example, the system 10 can be implemented at a central location and receive input/send results to a remote location (e.g., an individual medical facility). However, these examples are non-limiting, and the system 10 can be implemented in any combination of central and local implementation.

The one or more computing devices can include at least a non-transitory memory 12 (e.g., one or more non-transitory/hardware memory/storage devices) and a processor 14 (e.g., one or more hardware processors). The one or more computing devices can include additional components that are not illustrated, like a communication portal (that facilitates wired transmission and/or wireless transmission of data), a display device (that facilitates audio and/or visual display of at least the output), as well as additional components. The non-transitory memory 12 can be configured to store instructions to implement at least a receiver 16 and a determiner 18 (and may be used to implement more/alternative functionality), as well as data (which can include the data that is input and/or output). The processor 14 can be configured to access the non-transitory memory 12 and execute the instructions to implement the receiver 16 and the determiner 18 (and may be used to implement more/alternative functionality).

Upon execution, the receiver 16 can receive at least one imaging data set and at least one physiological data set and the determiner 18 can output at least the ideal parameter related to the LVAD based on at least the at least one imaging data set and the at least one physiological data set. In some instances, the determination of the ideal parameter can be further based on one or more hemodynamic data/variables related to the patient (e.g., systolic blood pressure, diastolic blood pressure, mean arterial blood pressure, heart rate, pulmonary capillary wedge pressure, etc). The ideal parameter can be displayed as an audio display and/or a visual display by the display device.

Figure 2:
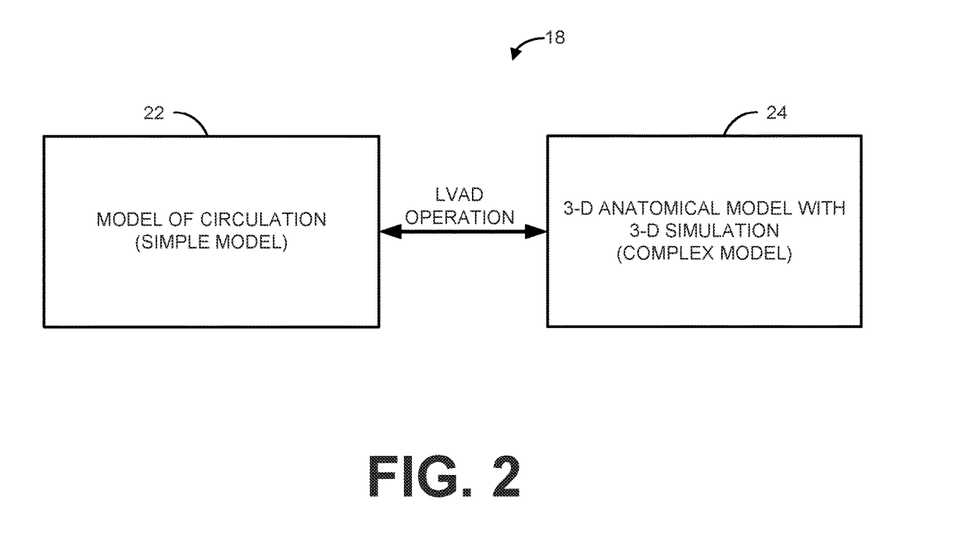
FIG. 2 is an example of two models that work together to allow the system of FIG. 1 to determine flow through the LVAD.

As shown in FIG. 2, the determiner 18 can execute a model of circulation (simple model) 22 and a 3-D anatomical model with 3-D simulation (complex model) 24. The simple model 22 has a short time course, while the complex model may have a longer time course (which can be shortened by simplifying the 3-D anatomical model to have fewer components). Output of the simple model 22, as well as parameters related to LVAD operation and/or anatomical/flow parameters, can be input into the complex model 24 and the complex model 24 can determine the ideal parameter. The simple model 22 can be a model of a region of a patient's body, which may be a large spatial region. For example, the large spatial region can include at least a portion of the patient's circulatory system (e.g., at least one atrium, at least one ventricle, a pulmonary vein, an aorta, and/or at least one branch of the aorta/pulmonary vein). The complex model 24 can be a 3-D anatomical model of at least one component of the region of the patient's body and at least one component of the LVAD. For example, the 3-D anatomical model can include at least one atrium, at least one ventricle, an aorta, and/or at least one branch of the aorta, the pulmonary vein and/or at least one branch of the pulmonary vein, and the at least one component of the LVAD can include an inflow cannula of the LVAD and/or an outflow cannula of the LVAD. Flow patterns within the complex model 24 can be calculated using computational fluid dynamics (CFD). As an example, CFD can be used also to assess wall shear stress, shear rate and blood stagnation, known risk factors for LVAD-related morbidity. Ultimately, the flow patterns can be calculated for one or more stages of the cardiac cycle under different patient conditions (e.g., rest vs. exercise). The complex model 24 can be used to study the flow patterns in humans supported by LVAD under varying LVAD parameters and varying human parameters.

Figure 3:
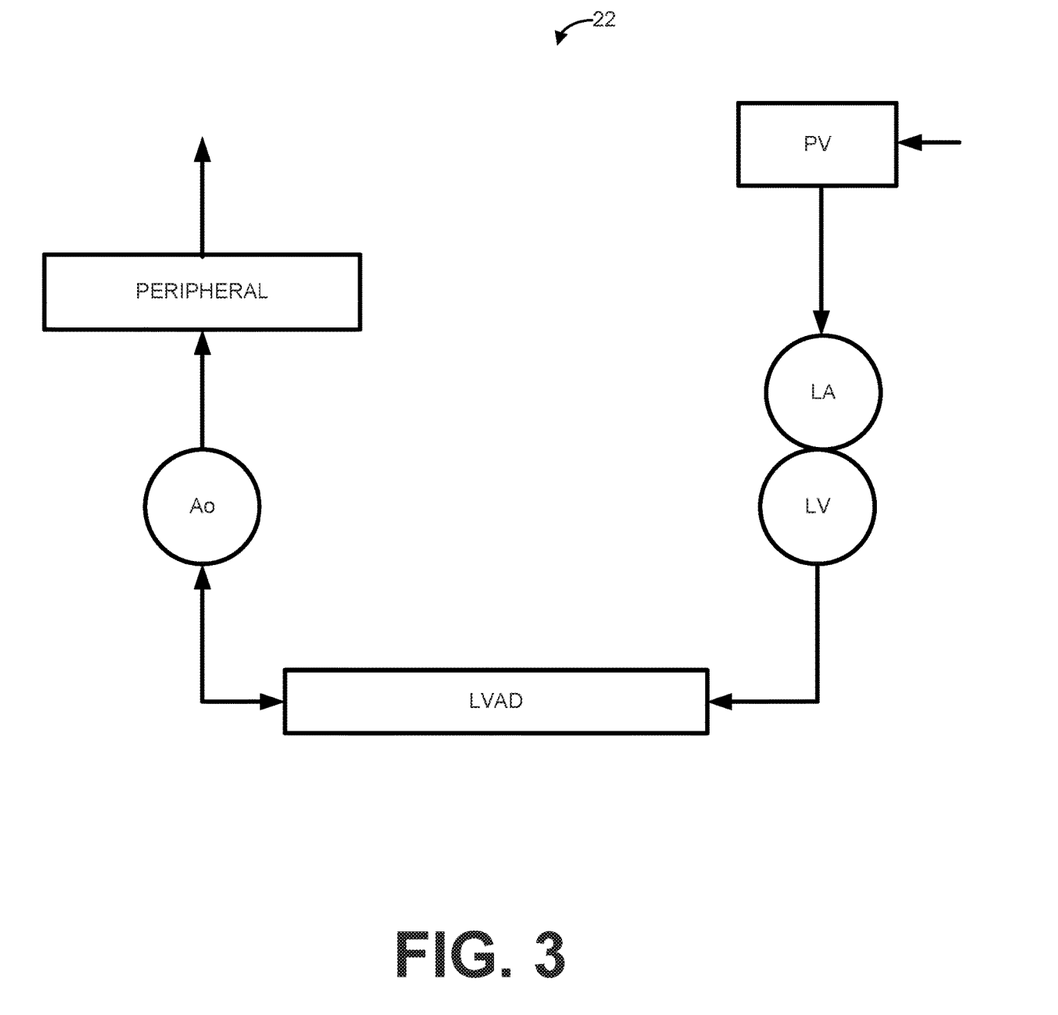
FIG. 3 is an example implementation of the model of circulation of FIG. 2.
Figure 4:
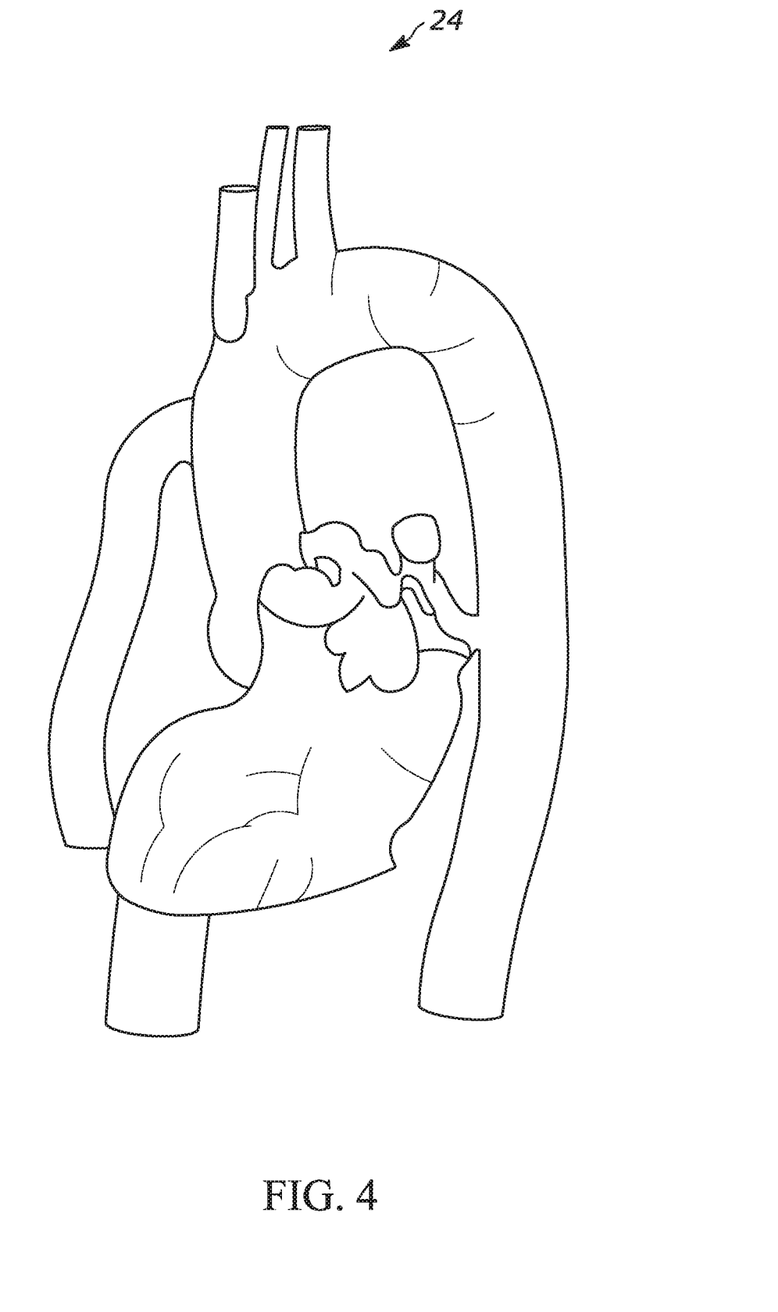
FIG. 4 is an example implementation of the 3D anatomical model with 3-D simulation of FIG. 2.

FIGS. 3-4 show a non-limiting practical example of the simple model 22 (FIG. 3) and the complex model 24 (FIG. 4). In this example, the simple model 22 uses models of the circulation through the cardiovascular system (although the electrical circuit analogy is not the only way to model the circulation) that includes the flow circuit from the pulmonary vein (PV) (which receives blood from the lungs), the left atrium (LA), the left ventricle (LV), the aorta (Ao) (which sends blood through the body (Peripheral)), and the LVAD. The simple model 22 can be personalized for the patient through clinical data (e.g., the imaging data set and physiological data set). For example, the simple model 22 can be represented as an electrical circuit, with vascular resistance and compliance represented as electrical resistors and capacitors, while the LVAD and ventricle are represented as power sources. The resistance, capacitance, and other parameters of each component can be calibrated such that the model performance (e.g., in terms of left atrial pressure) approximates the measured values of individual patients. The simple model 22 allows estimation of the physiological response to the LVAD operation, including different modes of operation like artificial pulsing. For example, once the model parameters are determined, LVAD operation mode can be varied to obtain the flow and pressure in the aorta as well as the ventricle, which can be fed to the complex model 24.

The complex model 24 includes a 3-D anatomical model and a 3-D model of at least a portion of the LVAD. The complex model 24 allows detailed description of the flow patterns and hemodynamic indicators (e.g., patterns of aortic valve opening due to LVAD operation mode). The computation of the complex model can be carried out at least in part by solving equations of fluid motion (e.g., Navier-Stokes equations) and mass conservation within the domain represented by the 3-D anatomical model (e.g., the aorta and ventricle, reconstructed from the imaging data set). The complex model 24 allows not only visualization and quantification of the pattern of flow under various LVAD operating modes but also realization of hypothetical scenarios in which the location and angle of the LVAD outflow cannula are varied, in order to identify the best-performing configuration of LVAD placement for an optimal circuit function (of the simple model 22). The simple model 22 and the complex model 24 can allow for more accurate assessment of periodic perturbations in flow patterns due to their dynamic nature, fully integrating pulsatile flow contributions from the left ventricle using a combination of measured data in addition to assumptions about the boundary conditions and force-length relationship from the image data set (which amounts to a model of an actual patient to be implanted with an LVAD or already with an implanted LVAD).

IV. Methods

Figure 5:
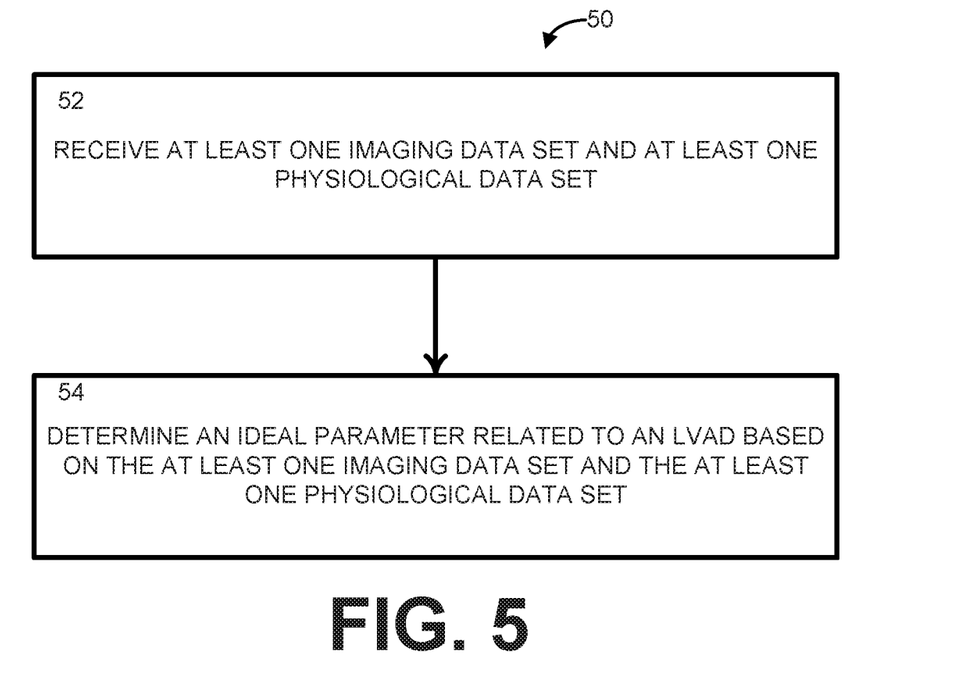
FIGS. 5 and 6 are process flow diagrams illustrating methods for modeling flow through an LVAD according to another aspect of the present disclosure.
Figure 6:
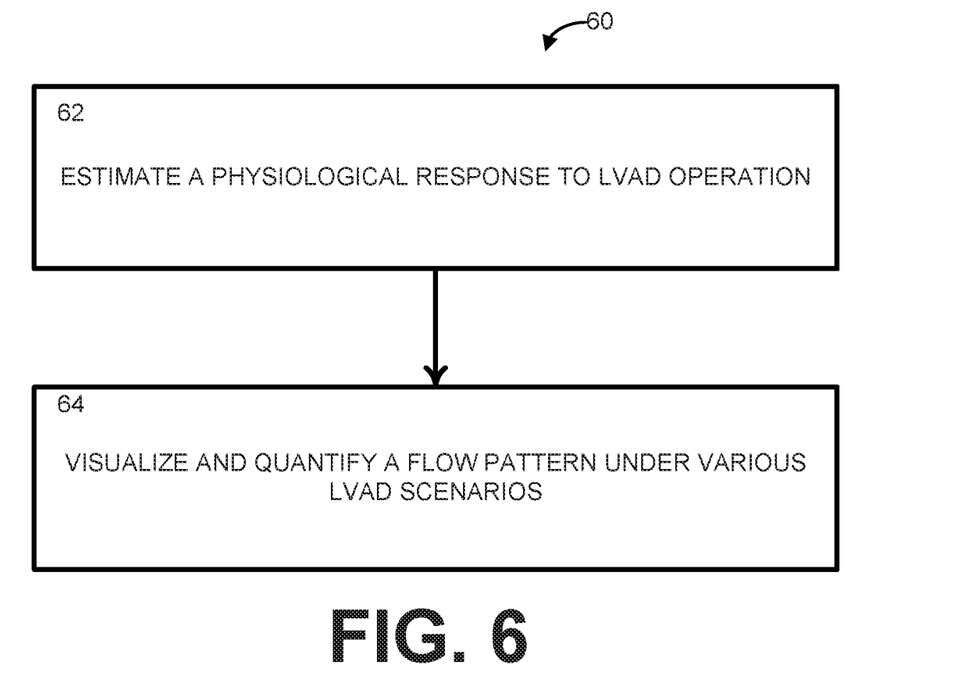

Another aspect of the present disclosure can include methods 50 and 60 for modeling flow through a left ventricular assist device (LVAD), as shown in FIGS. 5 and 6. The methods 50 and 60 can be executed using the system 10 shown in FIG. 1 (and the example models shown in FIG. 2).

For purposes of simplicity, the methods 50 and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60.

In some instances, one or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, some of the steps/acts can be implemented by a system comprising a processor that can access the computer-executable instructions that are stored in a non-transitory memory.

Referring now to FIG. 5, illustrated is an example of a method 50 for modeling flow through an LVAD. At Step 52, at least one imaging data set (e.g., a preoperative data set including pre-operative images, a post-operative data set including post-operative image, a data set including pre-operative images and post-operative images, etc.) and at least one physiological data set can be received. (e.g., by receiver 16 stored in non-transitory memory 12 and executed by processor 14). For example, the at least one imaging data set can be from a computed tomography (CT) scan and the at least one physiological data set can be from an echocardiogram (ECG). In a more specific example, the image data set can include one or more images of at least a portion of a cardiovascular system of the patient (e.g., a heart computed tomography data set) and the physiological data set can include ECG data from the patient. Additional data can also be input related to the patient and/or the LVAD.

At Step 54, an ideal parameter related to an LVAD can be determined (e.g., by determiner 18 stored in non-transitory memory 12 and executed by processor 14) based on the at least one imaging data set and the at least one physiological data set. In some instances, the determination of the ideal parameter can be further based on one or more hemodynamic data/variables related to the patient (e.g., systolic blood pressure, diastolic blood pressure, mean arterial blood pressure, heart rate, and pulmonary capillary wedge pressure). The ideal parameter can be used for preoperative planning of implantation of the LVAD into a patient and/or optimization of the LVAD after implantation into the patient. For example, the ideal parameter can include a position of an inflow cannula of the LVAD, an angle of the inflow cannula of the LVAD, a position of the outflow cannula of the LVAD, an angle of the outflow cannula of the LVAD, and/or at least one parameter related speed associated with the LVAD. As another example, the ideal parameter can indicate a value of concomitant valve surgery at the time of implantation of the LVAD.

Referring now to FIG. 6, illustrated is a method 60 for determining the ideal parameter (this method 60 can, for example, be executed by determiner 18 stored in non-transitory memory 12 and executed by processor 14). The ideal parameter can be determined using (1) a model of circulation in a large spatial region of the patient's body (e.g., which can include at least a portion of the patient's circulatory system) and (2) a three-dimensional anatomical model of at least one component of the region of the patient's body (e.g., which can include an atrium (left and/or right), a ventricle (left and/or right), an aorta, and/or at least one branch of the aorta) and at least one component of the LVAD (e.g., which can include an inflow cannula of the LVAD and/or an outflow cannula of the LVAD). The three-dimensional anatomical model may be customized based on a change in at least one parameter of the LVAD to determine the ideal parameter. Flow patterns within the three-dimensional anatomical model can be calculated using computational fluid dynamics (CFD). In some instances, the CFD calculation can account for the at least one hemodynamic parameter when calculating the flow patterns.

Execution of the two models can result in the method 60. Upon execution of the model of circulation, the simple model (1), at 62, a physiological response to LVAD operation can be estimated. At 64, upon execution of the more complex model (2), the three-dimensional anatomical model, a flow pattern can be visualized and quantified under various LVAD scenarios (e.g., different LVAD model, different placement of one or more components, different mode of operation, different speed, etc.). The ideal parameters under the various LVAD scenarios can be output (e.g., as an audio output by a speaker and/or a visual output on a display)

V. Exampies

The following example describes results of (1) a study of pump-patient interaction in a patient supported by a left ventricular assist device (LVAD), resulting in flow algorithms that fully incorporate left ventricular contractility and (2) a study of execution of the flow algorithms for a patient theoretically implanted with different LVAD devices/parameters. The following example is for the purpose of illustration only is not intended to limit the scope of the appended claims.

Methods

Patient Selection

From an LVAD cohort of patients at Medstar Washington Hospital Center, a patient was identified with concurrent contrast four-dimensional CT images and a complete hemodynamic assessment by right heart catheterization. This patient received HeartMate II (HMII, Abbott, Chicago, Ill.) in 2015. This research project has received IRB approval.

Computational Fluid Dynamic Modeling

A computational model framework to achieve personalized performance prediction of the cardiovascular system including LVAD was developed. The overall concept was centered around a computational model of the flow circuit, from left atrium and ventricle, LVAD and aorta. The model is personalized for each patient by reflecting information acquired through routine clinical measurements, hemodynamic measurements and gated imaging.

In the current form, detailed anatomical information was introduced in the model by means of high-resolution, four-dimensional CT images together with pulmonary capillary wedge pressure tracings from right heart catheterization. Additional patient specific variables incorporated to calibrate the model included blood pressure and heart rate as well as hematocrit and blood protein level (total and albumin) to estimate patient-specific non-Newtonian blood viscosity.

Figure 7:
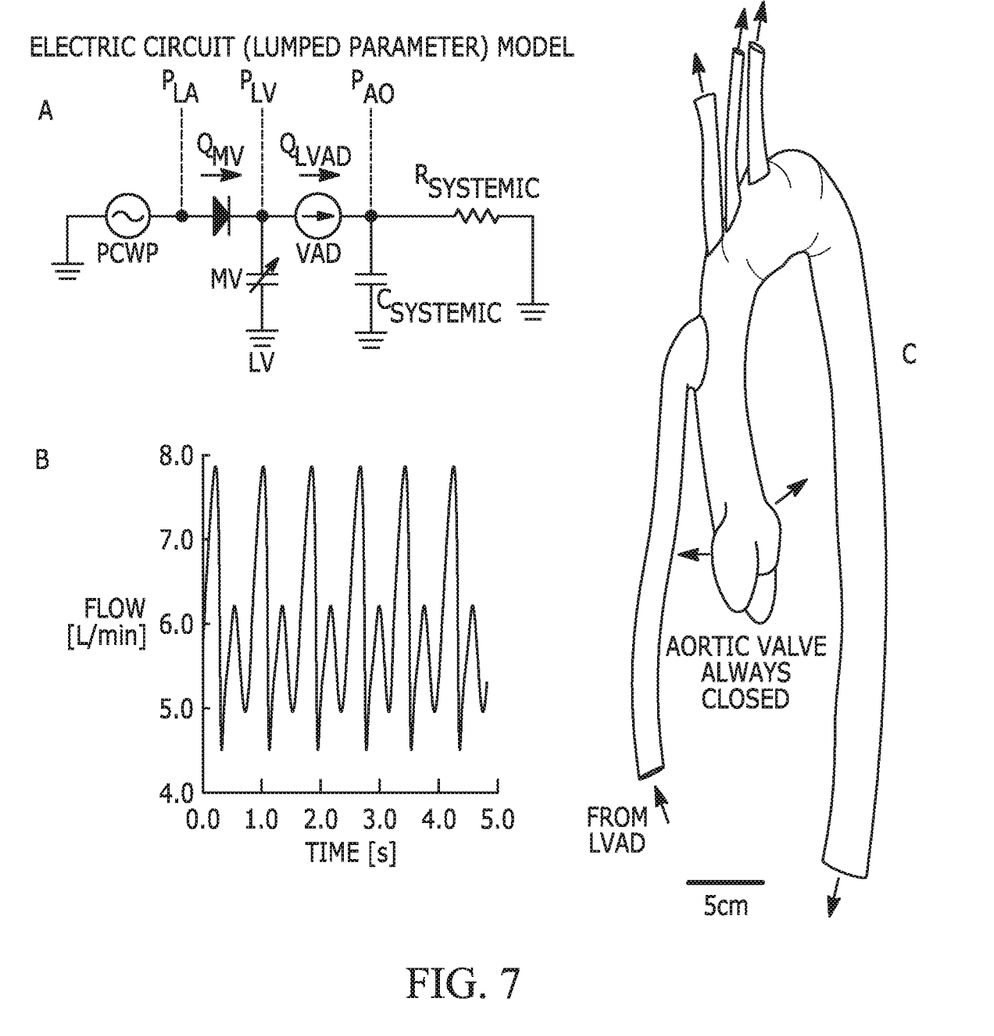
FIG. 7 shows an overview of the computational model used to determine flow through the LVAD, utilizing an electric circuit as the simple model.

The actual model was constructed in two steps: model of circulation using (1) electrical circuit analogy (shown in FIG. element A, electrical circuit lumped parameter model) and (2) three-dimensional (3D) CFD (shown in FIG. 7, element C, 3-D aortic anatomical model with LVAD outflow cannula). The former allows estimation of physiological response to the LVAD operation, including different modes of operation such as artificial pulsing, and the latter allows detailed depiction of flow patterns and hemodynamic indicators such as wall shear stress to evaluate the performance of the LVAD in terms of its potential impact on the physiologic system. In the electrical circuit analogue model, vascular resistance and compliance are represented by the electrical resistance and capacitance; each of LVAD and ventricle are represented by a power source.

The resistance, capacitance and other parameters of each component were calibrated such that the model performance (e.g. in terms of left atrial pressure) approximated well the measured values (e.g. pulmonary capillary wedge pressure for the left atrial pressure). Once the model parameters were determined, LVAD operation modes were varied to obtain the flow and pressure in the aorta as well as left ventricle (LV) (e.g., FIG. 7, element B, LVAD outflow waveform calculated from the model), which were then fed into the 3D model.

The 3D model computation was carried out by solving equations of fluid motion (Navier-Stokes equations) and mass conservation in the spatial domain of the aorta, reconstructed from high-resolution CT images. This model allows not only visualization and quantification of the pattern of flow under various LVAD operating modes but also realization of hypothetical scenarios related to outflow cannula geometry (diameter) or LVAD flow control algorithms in order to identify the best-performing configuration of the LVAD for an optimal circulatory function.

Variation of LVAD Type and Flow Algorithm

Figure 8:
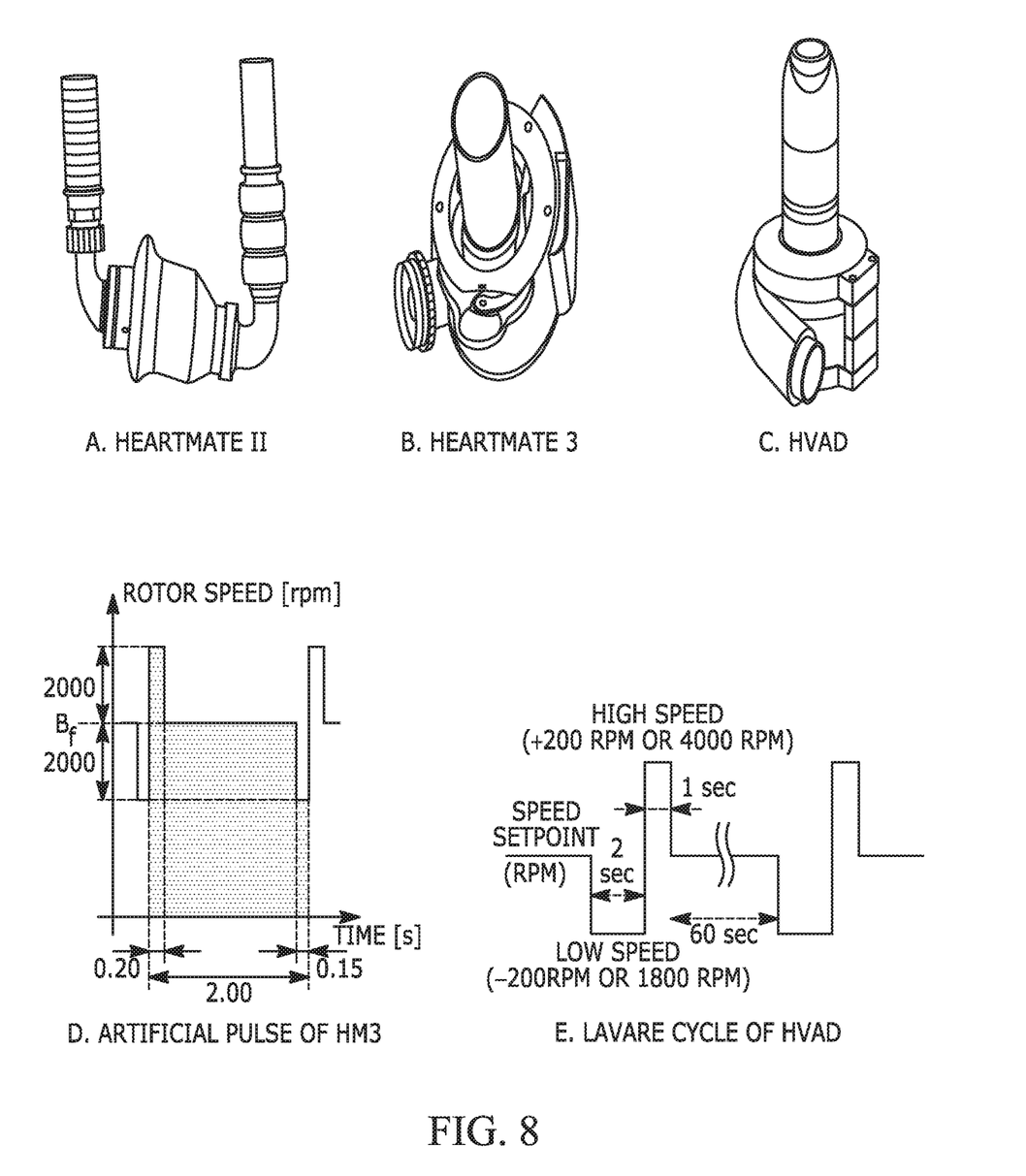
FIG. 8 shows different ventricular assist devices and modes that can be incorporated into the model.

Based on the anatomical model of the patient with a HMII (FIG. 8, element A), simulations were carried out for hypothetical scenarios substituting HeartWare HVAD (Medtronic, Minneapolis, Minn.) (FIG. 8, element B) with and without the Lavare cycle, HeartMate 3 (HM3, Abbott, Chicago Ill.) in continuous mode (FIG. 8, element C) and HM3 with Artificial Pulse operation mode (FIG. 8, element D). The anatomical model of the patient, reconstructed from CT images as described earlier, was kept unchanged for HM3 whereas the outflow cannula diameter was reduced from 14 mm to 10 mm for the HVAD case. For all the cases, the LVAD outflow was calculated first using a lumped-parameter model (LPM) of the systemic circulation including LVAD and used as the inflow boundary condition to the outflow cannula. The LPM of the systemic circulation was calibrated to the patient based on the patient-specific ventricular volume change reconstructed from four-dimensional CT, aortic pressure and pulmonary capillary wedge pressure tracings. The LVADs were implemented in the LPM via published H-Q curves in the continuous mode at 9000 RPM, 5500 RPM and 2600 RPM for HMII, HM3 and HVAD, respectively. The operational condition for HMII is for the actual patient and those for HM3 and HVAD are standard for producing 5.5 L/min flow against 60 mmHg pump head.

Additional to the continuous mode of operation, two commercially-available pulsatile flow conditions were tested: Artificial pulse operation mode for HM3 (FIG. 8, element D) and Lavare cycle (conditional flow pattern) operation mode for HVAD (FIG. 8, element E). Artificial pulse was incorporated by controlling the operating condition ±2000 RPM for short duration (0.15 s reduction and 0.2 s increase) every 2 seconds. Lavare cycle was incorporated by controlling the operation condition ±200 RPM for moderate duration (2 s reduction and 1 s increase) every 60 seconds. Further, concepts of co-pulsation and counterpulsation were tested to investigate the impact of these conditions on the flow patterns. Here, the rotational speed was increased by 200 RPM during systole (0-30% of the cycle) and diastole (50%-80% of the cycle), respectively.

In order to quantify the flushing effect in the aorta, virtual contrast agent was released in the ascending aorta and its flushing over the cycles was quantified. Shear stress acting on the aortic endothelium and shear rate in the blood stream were also quantified as indicators of normal/abnormal blood flow, especially the latter being a biomarker of platelet activation and hemolysis. Throughout the simulations, the aortic valve was kept closed, which reflects the clinical observation in this specific case.

Results

Figure 9:
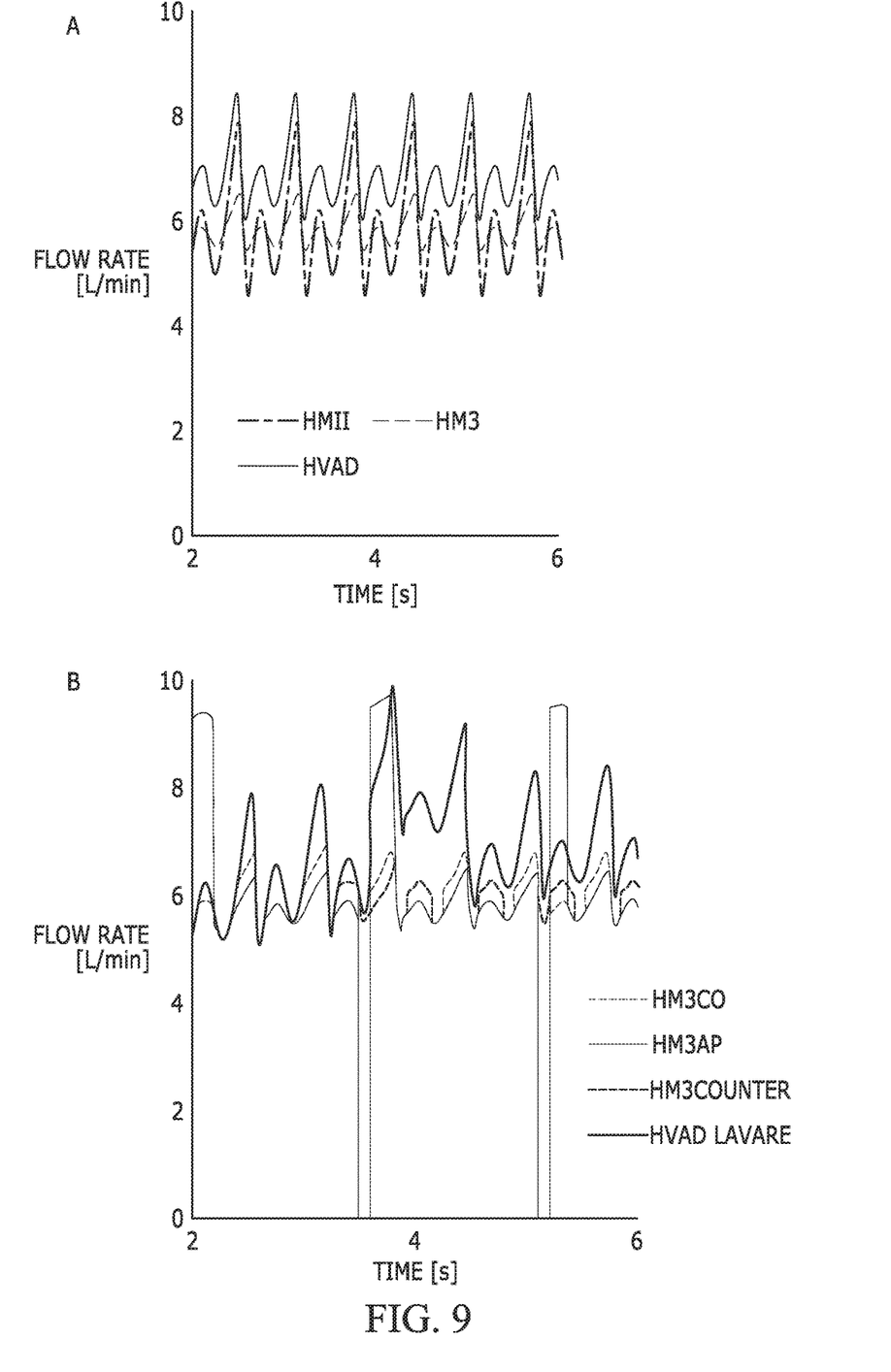
FIG. 9 shows predicted LVAD outflow waveforms.
Figure 10:
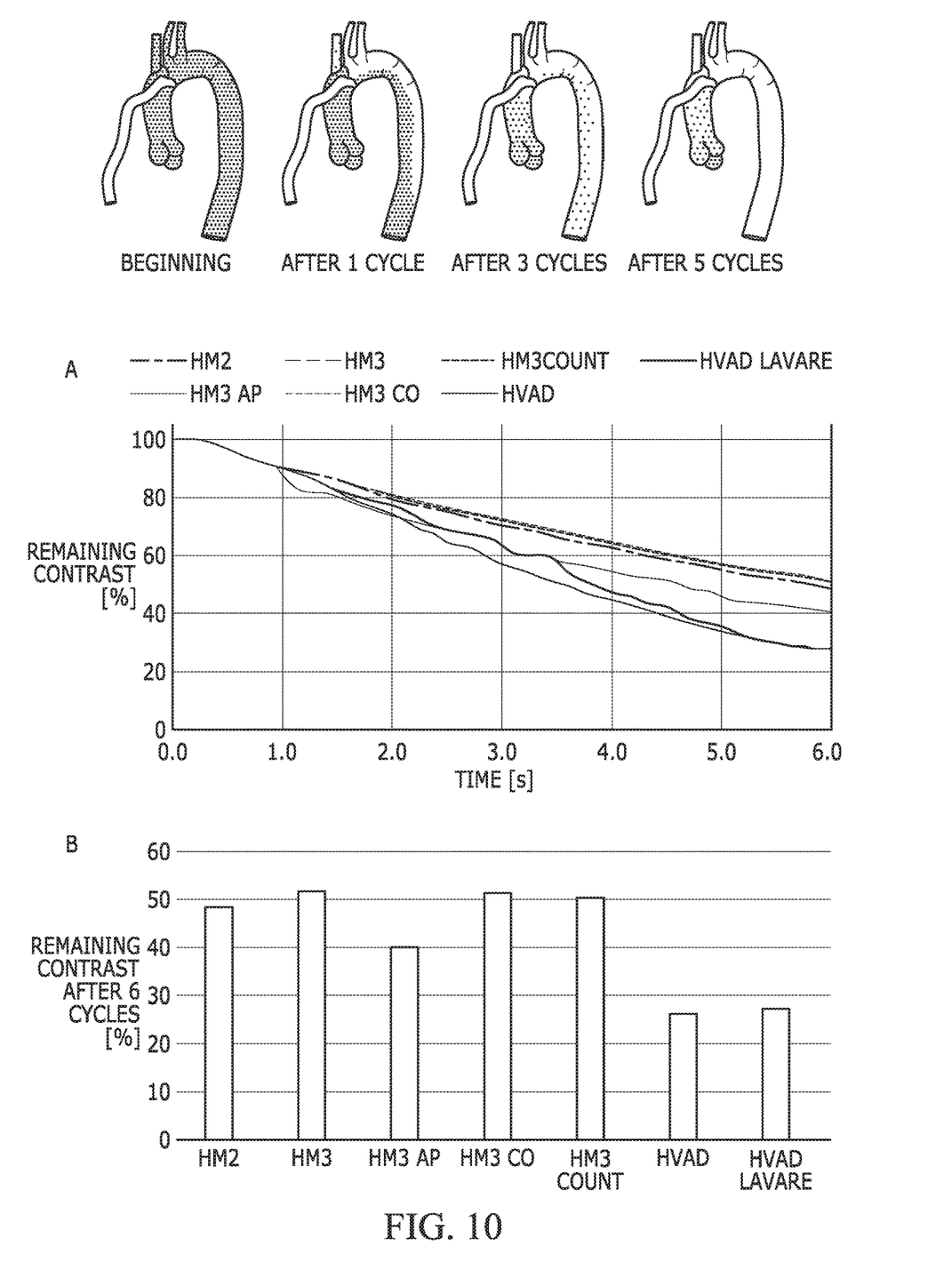
FIG. 10 shows an example of virtual contrast agent flushing.

Under standard operation conditions of the LVADs (9000 RPM for HMII, 5500 RPM for HM3 and 2600 RPM for HVAD), the mean flow rates were 5.81 L/min, 5.83 L/min and 6.85 L/min, for HMII, HM3 and HVAD, respectively (FIG. 9, element A, continuous modes). The velocity of blood flow in the outflow cannula was higher in the HVAD than in the two HeartMate pumps with a cycle average (range) of 0.92 m/s (range 0.78-1.19 m/s), 0.91 m/s (range 0.86-1.00 m/s) and 1.70 m/s (range 1.52-2.05 m/s) for HMII, HM3 and HVAD, respectively. Artificial pulse increased the peak flow rate to 9.80 L/min for the HM3 but the overall mean flow rate was 5.65 L/min, which was similar to the continuous mode (FIG. 9, element B, non-continuous modes). The flushing of blood from the ascending aorta was better for HVAD cases, with approximately 28% of blood remaining after 6 seconds. For the HM3, the addition of the artificial pulse markedly decreased blood stagnation in the ascending aorta; after 6 seconds (7.5 cardiac cycles), 49% of the blood was flushed out from the ascending aorta under the continuous operation mode while 60% was flushed under artificial pulse (FIG. 10, elements A and B).

Shear stress was greater with the HVAD when compared to the HMII or HM3. In the aortic arch and cerebral head vessels, a 64% increase in shear stress was noted with the HVAD compared to the HM3 in continuous mode (2.18 vs. 1.33 Pa). By comparison, the HVAD led to a 157% increase in shear stress in the ascending aorta (0.507 vs. 0.197 Pa). The addition of the artificial pulse to the HM3 flow algorithm led to a 48% increase in shear stress (0.291 vs 0.197 Pa) throughout the ascending aorta. On the contrary, the differences of shear stress due to the mode of operations, i.e. continuous mode vs non-continuous modes, was small with the maximum difference of 6% in the ascending aorta between continuous vs Artificial Pulse of HM3 (1.49 Pa vs 1.58 Pa).

Shear rate was elevated throughout the entirety of the thoracic aorta, particularly in the outflow cannula, in the HVAD model compared to the HM3 in continuous mode. Shear rate in the outflow cannula of HVAD cases are 325% higher than the cases with HM2 and HM3 (approximately 500 vs 155 s−1). The blood volume exposed to shear rate 1000 s−1 is also markedly higher for LVAD cases, approximately 2 cm3 (1% of total aortic volume) is exposed to the high shear rate whereas such volume is 1/10 in the other cases.

From the above description, those skilled in the art will perceive improvements, changes and modifications. Such improvements, changes and modifications are within the skill of one in the art and are intended to be covered by the appended claims.

The following is claimed:

1. A method comprising:
    receiving, by a system comprising a processor, at least one imaging data set related to a patient and at least one physiological data set related to the patient;
    executing, by the system, a two dimensional model of circulation in a large spatial region of the patient's body based on the at least one imaging data set related to the patient and the at least one physiological data set related to the patient for at least two different left ventricular assist device (LVAD) operating modes;
    outputting, by the system, from the two dimensional model a physiological response of at least one component of the large spatial region of the patient's body in response to the at least two different LVAD operating modes;
    executing, by the system, a three dimensional model of the at least one component of the large spatial region of the patient's body and at least a component of an LVAD within the at least one component of the large spatial region based on the physiological response of the at least one component of the large spatial region, the at least one imaging data set related to the patient, and the at least one physiological data set related to the patient using computational fluid dynamics (CFD) and varied pulsatile flow conditions corresponding to the at least two different LVAD operating modes;
    providing, by the system, one or more outputs related to flow patterns through the LVAD device and the at least one component of the large spatial region based on the CFD of executed three dimensional models with the at least one of varied pulsatile flow conditions of the at least one component, the at least two LVAD operating modes, and varied LVAD parameters;
    determining, by the system, an ideal parameter related to the LVAD based on comparisons of the one or more outputs of the three dimensional model; and
    outputting to an output device, by the system, the ideal parameter and an optimal LVAD position and/or an optimal LVAD setting for optimal circulatory functioning of the patient based on the ideal parameter.

2. The method of claim 1, wherein the large spatial region of the patient's body comprises the patient's circulatory system.

3. The method of clam 1, wherein the at least one component of the region comprises at least one of: an atrium, a ventricle, an aorta, and at least one branch of the aorta, and wherein the at least one component of the LVAD comprises an inflow cannula of the LVAD and/or an outflow cannula of the LVAD.

4. The method of claim 1, wherein the CFD calculation accounts for at least one hemodynamic parameter when calculating the flow patterns.

5. The method of claim 1, wherein the at least one imaging data set comprises at least a portion of a cardiovascular system of the patient; and wherein the at least one physiological data set is related to the cardiovascular system of the patient.

6. The method of claim 5, wherein the at least one imaging data set comprises a heart computed tomography data set; and
    wherein the at least one physiological data set comprises an echocardiogram.

7. The method of claim 1, wherein the at least one imaging data set comprises a pre-operative image of the patient and/or a post-operative image of the patient.

8. The method of claim 1, wherein the ideal parameter comprises at least one of: a position of an inflow cannula of the LVAD, an angle of the inflow cannula of the LVAD, a position of the outflow cannula of the LVAD, an angle of the outflow cannula of the LVAD, and at least one parameter related to a speed associated with the LVAD within the patient.

9. The method of claim 1, wherein the ideal parameter indicates a value of concomitant valve surgery at the time of implantation of the LVAD.

10. The method of claim 1, wherein the three-dimensional anatomical model is customizable based on a change in at least one parameter of the LVAD to determine the ideal parameter.

11. A system comprising:
a non-transitory computer readable medium storing instructions; and
a processor configured to access the non-transitory computer readable medium and execute the instructions to at least:
receive at least one imaging data set of a portion of a patient's anatomy and at least one physiological data set related to clinical measurements of the patient;
execute a two dimensional model of circulation in a large spatial region of the patient's body comprising at least an aorta and a left ventricle based on the at least one imaging data set related to the patient and the at least one physiological data set related to the patient, wherein the two dimensional model of circulation uses an electrical circuit analogy;
output estimations of flow and pressure in the aorta and the left ventricle of the patient for a plurality of varied left ventricular assist device (LVAD) operating parameters to evaluate performance of the LVAD in terms of potential impact on the patient's physiology;
execute a three dimensional model of at least one component of the large spatial region of the patient's body and at least one component of the LVAD within the at least one component of the large spatial region based on the output estimations of flow and pressure from the two dimensional model, the at least one imaging data set of the portion of the patient's anatomy, and the at least one physiological data set related to the clinical measurements of the patient;
output a plurality of flow patterns from the three-dimensional model of the at least one component of the large spatial region of the patient's body and the at least one component of the LVAD within the at least one component of the large spatial region that are calculated by computational fluid dynamic calculations using the plurality of varied LVAD operating parameters, varied LVAD component parameters, and varied pulsatile flow conditions;
determine an ideal parameter related to the LVAD by comparing the plurality of flow patterns for optimal circulatory function of the patient; and
output to an output device, by the system, the ideal parameter and an optimal LVAD position and/or an optimal LVAD setting for the optimal circulatory functioning of the patient based on the ideal parameter.

12. The system of claim 11, wherein the large spatial region of the patient's body comprises the patient's circulatory system.

13. The system of claim 11,
wherein the at least one component of the LVAD comprises an inflow cannula of the LVAD and/or an outflow cannula of the LVAD.

14. The system of claim 11, wherein the ideal parameter is determined further based on hemodynamic data related to the patient, wherein the hemodynamic data comprises at least one of systolic blood pressure, diastolic blood pressure, mean arterial blood pressure, heart rate, and pulmonary capillary wedge pressure.

15. The system of claim 11, wherein the at least one imaging data set of the portion of the patient's anatomy comprises at least a portion of a cardiovascular system of the patient; and
wherein the at least one physiological data set is related to the cardiovascular system of the patient.

16. The system of claim 15, wherein the at least one imaging data set of the portion of the patient's anatomy comprises a heart computed tomography data set; and
wherein the at least one physiological data set comprises an echocardiogram.

17. The system of claim 11, wherein the at least one imaging data set of the portion of the patient's anatomy comprises a pre-operative image of the patient and/or a post-operative image of the patient.

18. The system of claim 11, wherein the ideal parameter comprises at least one of: a position of an inflow cannula of the LVAD, an angle of the inflow cannula of the LVAD, a position of the outflow cannula of the LVAD, an angle of the outflow cannula of the LVAD, and at least one parameter related to a speed associated with the LVAD within the patient.

* * * * *